United States Patent [19]  [11] Patent Number: 4,897,388
Malluche  [45] Date of Patent: Jan. 30, 1990

[54] METHOD OF TREATING ALZHEIMER'S DISEASE

[75] Inventor: Hartmut H. Malluche, Versailles, Ky.

[73] Assignee: Geriatric Research Institute, Inc., Brookfield, Wis.

[21] Appl. No.: 287,754

[22] Filed: Dec. 20, 1988

[51] Int. Cl.⁴ ............................................... A61K 31/59
[52] U.S. Cl. .................................................... 514/167
[58] Field of Search ......................................... 514/167

[56] References Cited

U.S. PATENT DOCUMENTS

| 4,230,701 | 10/1980 | Holick et al. | 514/167 |
| 4,385,053 | 5/1983 | Reisberg et al. | 424/199 |
| 4,419,365 | 12/1983 | McLachlan | 424/320 |
| 4,663,318 | 5/1987 | Davis | 514/215 |
| 4,758,430 | 7/1988 | Sabin | 424/94.1 |

Primary Examiner—Stanley J. Friedman
Attorney, Agent, or Firm—Quarles & Brady

[57] ABSTRACT

The method of treating Alzheimer's disease which comprises administering to a patient having the disease a safe and effective amount of a biologically active vitamin $D_3$ or $D_2$ material.

3 Claims, No Drawings

METHOD OF TREATING ALZHEIMER'S DISEASE

FIELD OF THIS INVENTION

The present invention relates to a novel method of treating Alzheimer's disease and more particularly to a method of treatment employing biologically active vitamin $D_3$ and vitamin $D_2$ materials.

BACKGROUND OF THE INVENTION

Senile dementia affects approximately 1.5 million persons over age 65 in the U.S. The most common form is Alzheimer's disease. At the moment, it is a disease of unknown cause and unknown treatment. Any procedure or drug treatment that would slow down or reverse the progressive deterioration of the Alzheimer's disease patient would be a major plus for the patient, his/her family and society.

SUMMARY OF THE INVENTION

It is the primary object of the present invention to disclose a method of treating Alzheimer's disease.

The method of present invention of treating Alzheimer's disease comprises administering to a person requiring such treatment, a pharmaceutically acceptable biologically active vitamin $D_3$ or vitamin $D_2$ material. Such materials are administered orally, parenterally or topically. The dosage of materials depends upon the route of administration, the activity of the material and the individual condition of the patient and the stage of the disease.

In the past, biologically active vitamin $D_3$ and $D_2$ materials, due to their action in increasing serum calcium have been utilized in the treatment of various calcium metabolic disorders. Among these disorders include chronic renal disease, vitamin D resistant rickets, glucocorticord induced decrease in calcium absorption, osteoporosis, senile decrease in calcium absorption, hypoparathyroidism, turkey weak leg diseases, milk fever diseases, and the like. In the past, biologically active vitamin $D_3$ and vitamin $D_2$ materials have been administered to patients orally, intravenously and topically by contact with the skin of the patient which acts as a transport medium for the biologically active material.

A recent study in Japan has suggested that there is a positive correlation between serum parathyroid hormone levels and cognitive decline in Alzheimer patients and a negative correlation between parathyroid hormone levels and 1, 25 Vitamin D levels.

DETAILED DESCRIPTION

In accordance with the present invention, any conventional method of providing a biologically active vitamin $D_3$ or vitamin $D_2$ material to the individual can be utilized.

An especially preferred product for oral administration is calcitriol which is available from Roche Laboratories as ROCALTROL ®. It is a synthetic vitamin D analog which is active in the regulation of the absorption of calcium from the gastrointestinal tract and its utilization in the body. Calcitriol is a colorless, crystalline compound which occurs naturally in humans. It is commercially available as 0.25-mcg and 0.5-mcg soft gelatin capsules for oral administration. It has a calculated molecular weight of 416.65 and is soluble in organic solvents but relatively insoluble in water. Chemically, calcitriol is 9,10-seco(5Z,7E)-5,7,10 (19)-cholestatrien-1$\alpha$,3$\beta$,25-triol. The other names frequently used for calcitriol are 1$\alpha$,25-dihydroxycholecalciferol, 1,25-dihydroxyvitamin $D_3$, 1,25-DHCC, 1,25(OH)$_2$D$_3$ and 1,25-diOHC.

Calcitriol is rapidly absorbed from the intestine. Peak serum concentrations (above basal values) were reached within 3 to 6 hours following oral administration of single doses of 0.25 to 1.0 mcg of calcitriol. The half-life of calcitriol elimination from serum was found to range from 3 to 6 hours. Following a single oral dose of 0.5 mcg, mean serum concentrations of calcitriol rose from a baseline value of 40.0±4.4 (S.D.) pg/ml to 60.0±4.4 pg/ml at 2 hours, and declined to 53.0±6.9 at 4 hours, 50±7.0 at 8 hours, 44±4.6 at 12 hours and 41.5±5.1 at 24 hours. The duration of pharmacologic activity of a single dose of calcitriol is about 3 to 5 days.

Calcitriol is indicated in the management of hypocalcemia in patients undergoing chronic renal dialysis. In studies to data, it has been shown to reduce elevated parathyroid hormone levels in some of these patients.

Calcitriol should not be given to patients with hypercalcemia or evidence of vitamin D toxicity. The recommended initial dose of calcitriol is 0.25 mcg/day given in the morning. If a satisfactory response in the biochemical parameters and clinical manifestations of the disease is not observed, the dose may be increased at two-to four-week intervals. During the dosage titration period, serum calcium levels should be obtained at least twice weekly and, if hypercalcemia is noted, calcitriol should be immediately discontinued until normocalcemia ensues. Careful consideration should also be given to lowering the dietary calcium intake.

Most adult patients should respond to dosages in the range of 0.5 to 2 mcg daily.

EXAMPLE

A patient suffering from Alzheimer's disease is given 0.5 mcg of calcitriol (Rocaltrl) daily for 7 days at which time an improvement in the patient's condition is apparent.

In some cases, the topical route of application may be preferred. Among the preferred topical methods are included the procedure whereby the provitamin of or the previtamin of the biologically active vitamin $D_2$ or $D_3$ material is topically applied to the skin. Another preferred method is to apply the biologically active vitamin $D_3$ or $D_2$ material of the skin itself. Any conventional method of topical application or conventional topical preparation can be utilized to apply either the provitamin or previtamin of the biologically active vitamin $D_3$ or $D_2$ material or even the biologically active vitamin $D_2$ or $D_3$ material itself to the skin. In the case where the biologically active vitamin $D_3$ or vitamin $D_2$ material is provided to the skin by the provitamin of the biologically active vitamin $D_2$ or $D_3$ materials, the provitamin is applied topically to the skin and the skin is subjected to ultra-violet light radiation. The topical administration of these materials is described and claimed in the Holick et al. U.S. Pat. No. 4,230,701, which is incorporated by reference herein.

Among the preferred biological active vitamin $D_2$ and $D_3$ materials which are applied in accordance with this invention are the biological active metabolites and analogues of vitamin $D_2$ and vitamin $D_3$ as well as the corresponding provitamins and previtamins of these biologically active vitamin $D_2$ or $D_3$ metabolites or analogues.

Among the preferred provitamins of these biologically active vitamin $D_2$ or $D_3$ metabolites or analogues are included:

1α,25-dihydroxy-B 7-dehydrocholesterol[1α,25-(OH)$_2$ proD$_3$];
1α,24,25-trihydroxy-7-dehydrocholesterol[1α,24,25-(OH)$_3$ proD$_3$];
24,25-dihydroxy-7-dehydrocholesterol[24,25-(OH)$_2$-proD$_3$];
1α-hydroxy-7-dehydrocholesterol[1α-OHproD$_3$];
1α,24-dihydroxy-25-fluoro-7-dehydrocholesterol[-1α,24-(OH)$_2$ 25FproD$_3$];
25,26-dihydroxy-7-dehydrocholesterol[25,26-(OH)$_2$ proD$_3$];
25-hydroxy-7-dehydrocholesterol[25-(OH)proD$_3$];
25-hydroxy-ergosterol[25-OHproD$_2$]; and
1α,25-dihydroxy-ergosterol[1α,25-(OH)$_2$ proD$_2$].

Among the preferred previtamin $D_3$ metabolites are:

1α,25-dihydroxy-precholecalciferol[1α,25-(OH)$_2$-preD$_3$];
1α,24,25-trihydroxy-precholecalciferol[1α,24,25-(OH)$_3$preD$_3$];
24,25-dihydroxy precholecalciferol[24,25-(OH)$_2$-preD$_3$];
1α,-hydroxy-precholecalciferol[1α-(OH)preD$_3$];
1α,24-dihydroxy-25-fluoro-precholecalciferol[1α,24-(OH)$_2$ 25FpreD$_3$]; and
25-hydroxy-precholecalciferol[25-OHpreD$_3$].
1α-hydroxy-previtamin $D_2$ [1α-OHpreD$_2$];
25-hydroxy-previtamin $D_2$ [25-OHpreD$_2$] and
1α,25-dihydroxy-previtamin $D_2$ [1α,25-(OH)$_2$ preD$_2$].

The following biologically active vitamin $D_2$ and $D_3$ compounds are particularly preferred:
Dihydrotachysterol$_2$;
Dihydrotachysterol$_3$;
5,6-trans-vitamin $D_3$;
25-hydroxy-5,6-trans vitamin $D_3$;
1α-hydroxy vitamin $D_2$ [1α-OHD$_2$];
25-hydroxy vitamin $D_2$ [25-OHD$_2$];
1α,25-dihydroxy vitamin $D_2$ [1α,25-(OH)$_2$D$_2$].
1α,25-dihydroxy-cholecalciferol[1α,25-(OH)$_2$ D$_3$];
1α,24,25-trihydroxy-cholecalciferol[1α,24,25-(OH)$_3$D$_3$];
24,25-dihydroxy-cholecalciferol[24,25-(OH0$_2$D$_3$];
1α,24-dihyroxy-25-fluoro-cholecalciferol[1α,24-(OH)$_2$ 25FD$_3$];
25-hydroxy-cholecalciferol[25-OHD$_3$]; and
1α-hydroxy-cholecalciferol[1α-OHD$_3$].

Among these preferred vitamin $D_3$ compounds, the vitamin $D_3$ compound where the 24-hydroxy group has the R configuration is especially preferred. Also preferred are those 24,25-dihydroxy-vitamin $D_3$ compounds where the 24-hydroxy group has an R-configuration.

The aforementioned biologically active vitamin $D_2$ and $D_3$ materials, their corresponding previtamins and provitamins can be applied to the skin topically utilizing any conventional method for topically applying pharmaceuticals. In general, one application can contain at least 0.05 micrograms of the active material per administration. Generally, these materials can be applied in amounts of 0.5 to about 100 micrograms per administration with 0.1 to 10 micrograms per administration being preferred. In general, amounts of these biologically active vitamin $D_2$ or $D_3$ materials, i.e. either as the previtamin, vitamin or provitamin can be applied topically in doses of greater than 100 micrograms per administration. This is especially true since through the application of these materials to the skin, the amount of the biologically active vitamin $D_3$ or $D_2$ materials transported to the bloodstream is regulated and stored in the skin. Therefore, the danger of applying the biologically active vitamin $D_3$ or $D_2$ materials in excessive dosages is minimized through the controlled transport by the skin to the bloodstream.

The biologically active vitamin $D_2$ and $D_3$ materials as well as their previtamins and provitamins, can be applied to the skin through conventional methods. Any conventional topical preparation can be utilized to apply these materials to the skin. Any of the means conventional in applying pharmaceuticals in topical forms with conventional pharmaceutical carriers can be utilized in accordance with this invention. For topical administration, the biologically active vitamin $D_2$ and $D_3$ materials as well as their previtamins and provitamins can be conventionally prepared as ointments, tinctures, creams, gels, solutions, lotions, sprays, suspensions and the like. Ointments, creams and solutions are preferred.

The dosage to be administered will vary with the severity of the diseased condition. However, in general, particularly for oral administration, the administration of from 0.25 mcg/day to 2 mcg/day of calcitriol or its equivalent of another vitamin $D_3$ or $D_2$ biologically active material will usually be effective. Frequency of dosage administration may, of course, be varied as needed and as discretionarily required by the attending physician.

It will be readily apparent to those skilled in the art that a number of modifications and change may be made without departing from the spirit and scope of the invention. Therefore, the invention is not to be limited except by the claims.

I claim:

1. A method of treating Alzheimer's disease which comprises administering to a patient having the disease a safe and symptom-alleviating amount of a compound selected from the class consisting of:

1α,25-dihydroxy-7-dehydrocholesterol;
1α,24,25-trihydroxy-7-dehydrocholesterol;
24,25-dihyroxy-7-dehydrocholesterol;
1α-hydroxy-7-dehydrocholesterol;
1α,24-dihydroxy-25-fluoro-7-dehydrocholesterol;
25,26-dihydroxy-7-dehydrocholesterol;
25-hydroxy-7-dehydrocholesterol;
1α-hydroxy-ergosterol;
25-hydroxy-ergosterol;
1α,25-dihydroxy-ergosterol;
1α,25-dihydroxy-precholecalciferol;
1α,24,25-trihydroxy-precholecalciferol;
24,25-dihydroxy precholecalciferof;
1α,-hydroxy-precholecalciferol;
1α,24-dihydroxy-25-fluoro-precholecalciferol;
25-hydroxy-precholecalciferol;
1α-hydroxy-previtamin $D_2$;
25-hydroxy-previtamin $D_2$;
1α,25-dihydroxy-previtamin $D_2$;
Dihydrotachysterol$_2$;
Dihydrotachysterol$_3$;
5,6-trans-vitamin $D_3$;
25-hydroxy-5,6-trans vitamin $D_3$;
1α-hydroxy vitamin $D_2$;
25-hydroxy vitamin $D_2$;
1α,25-dihydroxy vitamin $D_2$;

calcitriol;
1α,24,25-trihydroxy-cholecalciferol;
24,25-dihydroxy-cholecalciferol;
1α,24-dihydroxy-25-fluoro-cholecalciferol;
25-hydroxy-cholecalciferol; and
1α-hydroxy-cholecalciferol.

2. A method of claim 1 in which the compound is calcitriol.

3. A method of claim 1 in which the compound is administered in the form of a topical preparation.

* * * * *